United States Patent [19]

Crane et al.

[11] Patent Number: 4,523,997

[45] Date of Patent: Jun. 18, 1985

[54] AFFINITY CHROMATOGRAPHY MATRIX WITH BUILT-IN REACTION INDICATOR

[75] Inventors: Laura J. Crane, Long Valley; Hugh E. Ramsden, Scotch Plains, both of N.J.

[73] Assignee: J. T. Baker Chemical Company, Phillipsburg, N.J.

[21] Appl. No.: 585,782

[22] Filed: Mar. 2, 1984

[51] Int. Cl.$^3$ ............................................ B01D 15/08
[52] U.S. Cl. ...................................... 210/635; 210/656; 210/502.1; 502/157; 502/402; 502/403
[58] Field of Search ...................... 210/635, 656, 198.2, 210/502.1; 502/157, 401, 402, 403, 404, 405, 509, 516; 55/67, 386

[56] References Cited

U.S. PATENT DOCUMENTS

| | | | |
|---|---|---|---|
| 3,892,678 | 7/1975 | Halasz | 502/401 |
| 4,212,905 | 7/1980 | Tsibris | 210/656 |
| 4,213,860 | 7/1980 | Tsibris | 210/656 |
| 4,334,972 | 6/1982 | Soderberg | 210/656 |

*Primary Examiner*—John Adee
*Attorney, Agent, or Firm*—George W. Rauchfuss, Jr.

[57] ABSTRACT p-Nitrophenylester of succinoylaminopropyl silica gel is useful as an affinity matrix for reacting with ligand for use in affinity chromatography. The affinity matrix, upon reaction with a ligand, releases one molecule of p-nitrophenolate ion for every molecule of ligand that reacts and the solution turns yellow as the reaction occurs.

6 Claims, No Drawings

AFFINITY CHROMATOGRAPHY MATRIX WITH BUILT-IN REACTION INDICATOR

FIELD OF THE INVENTION

This invention relates to the field of affinity chromatography and to affinity matrixes for use in affinity chromatography.

BACKGROUND OF THE INVENTION

Affinity chromatography is a separation technique based on specific and reversible molecular interactions between two biologically active substances. However, the development of affinity chromatography has been retarded to a great extent by the absence of suitable supports and the lack of satisfactory techniques for immobilizing ligands.

It is especially desirable that an affinity matrix be available for use in affinity chromatography which maxtrix has a leaving group, used as an activator for the coupling reaction with the ligand, which forms a reaction indicator in aqueous solutions.

BRIEF SUMMARY OF THE INVENTION

It has been found that the p-nitrophenylester of succinoylaminopropyl silica gel as an affinity matrix is particularly useful for reacting with ligands to produce an affinity matrix having a ligand covalently bound to the affinity matrix and useful in affinity chromatography to separate or purify a substance from a solution by reacting said substance in the solution with the affinity matrix having a ligand covalently bound to the affinity matrix. Additionally, it has been found that the use of the p-nitrophenylester of succinoylaminopropyl silica gel as an affinity matrix provides a matrix having a leaving group used as an activator for the coupling reaction with a ligand which leaving group forms a bright yellow anion in aqueous solution at pH > 7. Thus, this affinity matrix is highly beneficial in that it contains an activated reactive group with a built-in or internal reaction indicator.

DETAILS OF THE INVENTION

The novel affinity matrix of this invention is the p-nitrophenylester of succinoylaminopropyl silica gel of the general formula

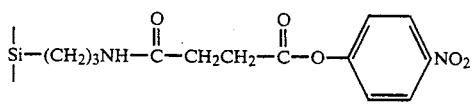

wherein

represents the silica gel. The p-nitrophenylester of succinoylaminopropyl silica gel is prepared by reacting p-nitrophenol with succinoylaminopropyl silica gel in the presence of dicylohexylcarbodimide.

The succinoylaminopropyl silica gel is commercially available or can be prepared, for example, from silica gel by reacting silica gel with aminopropyltriethoxysilane and reacting the product aminopropyl silica gel with succinic anhydride. Silica gel suitable for use in forming the matrix of this invention is any particulate silica gel having an average particle diameter of from about 3 to about 200 microns and an average pore size of from about 50 to about 1000 Angstrom units. Such silica gel, consisting of amorphous silica, is commercially available in irregular and spherical particulate forms. Where the affinity matrix product of this invention is to be used in chromatographic columns a silica gel of from about 3 to about 70 microns average diameter is generally employed whereas if the affinity matrix product of this invention is to be used in a batch separation medium, such as a test tube or the like, silica gel of from about 3 to about 200 microns average diameter can be employed.

The p-nitrophenylester of succinoxylaminopropyl silica gel affinity matrix of this invention can be used as an affinity matrix for binding to any ligand which covalently bonds to the affinity matrix. The affinity matrix is especially useful for reacting with ligands having reactive amino groups although it is also quite useful for reacting with ligands having other reactive groups such as for example ligands containing reactive hydroxyl, sulfhydryl and the like groups. The nitrophenyl ester of the matrix of this invention readily reacts with such a reactive groups of a protein, enzyme or other such ligand to yield the ligand immobilized on the silica gel matrix. As examples of ligands containing such reactive groups which can be immobilized on the affinity matrix of this invention by covalent binding thereto there can be mentioned for example antigens, antibodies, enzymes, inhibitors, cofactors, hormones, vitamins, toxins, growth factors, glycoconjugates, lectins, nucleic acids and proteins which are known in the art. The ligand bound affinity matrixes of this invention are employed to purify or separate substances, such as for example, proteins containing reactive amine groups, from solutions containing such substance by reacting the substance in solution with an affinity matrix of this invention having a ligand covalently bound to the affinity matrix. Among such substances to be separated or purified there can be mentioned, for example, trypsin, d-tryptophan methyl ester, m-aminobenzamidine, p-aminobenzyl-thio-N-acetyl-$\beta$-d-glucosamine, p-aminophenyllactic acid, phenylbutylamine and the like.

The p-nitrophenylester of succinoylaminopropyl silica gel affinity matrix of this invention has the special advantage that the leaving group used as the activator for the coupling reaction with the ligand forms a bright yellow anion in aqueous solutions at pH > 7. Therefore, as the ligand-matrix coupling reaction occurs, for every molecule of ligand that reacts, one molecule of p-nitrophenolate ion, absorption$\epsilon \sim$ 10,000 at 400 nm wavelength, is released and the solution turns yellow as the reaction occurs. At neutral pH's the p-nitrophenylester of succinoylaminopropyl silica gel is only very slowly reactive with water, and is very reactive with amine groups and other nucleophiles. Therefore, formation of yellow color is an accurate measure of the rate and extent of ligand reaction.

The affinity matrix of this invention and the use thereof to covalently bond to ligands is illustrated but not limited by the following examples.

Although succinoylaminopropyl silica gel is commercially available and could be used for the preparation of the affinity matrix of this invention, it is possible that the succinoylaminopropyl silica gel reactant can be prepared according to the following exemplary preparation.

PREPARATION

Fifty grams of silica gel (40 u, 650 A pore), was reacted with 22.5 grams of aminopropyltriethoxysilane in about 250 ml of toluene for about 20 hours. After filtration, the solid silica gel was washed with 200 ml of toluene twice, 200 ml of methanol twice and 200 ml of ethyl ether once. It was dried and heat treated at about 80° C. for about 4 hours, 43 minutes.

The aminopropyl silica gel product was mixed with 300 ml of toluene and 16 grams of succinic anhydride and rotated in a 40° C. bath for about 2½ hours, filtered, washed with 200 ml of toluene twice, 200 ml of methanol twice and 200 ml of ethyl ether once and oven dried.

Treatment of the succinoylaminopropyl silica gel produced with 15 ml of trimethylchlorosilane in 300 ml of toluene followed by filtration, washing and oven drying yielded a capped succinoylaminopropyl silica gel product with a titer of 0.3 meq of acid groups per gram.

EXAMPLE 1

15 grams of the succinoylaminopropyl silica gel product of the above Preparation was treated in about 114 ml of toluene and 7.5 ml of dry pyridine with 0.95 grams p-nitrophenol and 3.8 grams of dicyclohexyl carbodiimide and 0.2 g dimethylamino pyridine for about 2 hours, 18 minutes. The reaction mixture was filtered, washed with 100 ml of toluene twice, and with 100 ml of methanol twice, and then dried in an oven at 80° C. About 15.3 grams of the p-nitrophenylester of succinoylaminopropyl silica gel product resulted.

EXAMPLE 2

The p-nitrophenylester of succinoylaminopropyl silica gel affinity matrix of Example 1 was treated with 200 mg of trypsin dissolved in 60 ml of phosphate buffer (pH 7) on a shaker for about 4 hours and then about 62 ml of 0.1 M tris (trihydroxymethyl) aminomethane solution (pH 8.0) for about 3 hours. After filtration and washing with pH 7 buffer, it was stored in pH 7 buffer. Tested for activity, the product showed high trypsin activity.

EXAMPLE 3

In this example, the reaction of trypsin with the p-nitrophenylester of succinoylaminopropyl silica gel affinity matrix of this invention is monitored by following the absorbance of p-nitrophenol in the reaction supernatant. Concomitantly the extent of the reaction is measured by measuring the amount of trypsin remaining in the supernatant by measuring the absorbance of the solution at 2 nm wavelength. When the above two absorbance measurements were made, the absorbance at 280 nm of the trypsin in the supernatent, as compared with a suitable reagent blank, decreased rapidly to zero over the same time period as the absorbance of p-nitrophenol, measured at 400 nm increased to a maximum. Correlation of the two values which is shown by this example demonstrates the validity and usefulness of employing the release of p-nitrophenolate ion and the coloration of the aqueous solution thereby as an accurate measure of the rate and extent of ligand reaction with affinity matrix.

We claim:
1. The p-nitrophenylester of succinoylaminopropyl silica gel.
2. The product of claim 1 wherein the silica gel has an average particle diameter of from about 3 to about 70 microns and an average pore size of from about 50 to about 100 Angstrom units.
3. In a method of separating or purifying a substance from a solution by reacting the substance in the solution with an affinity matrix having a ligand covalently bound to the affinity matrix, the improvement comprising employing the p-nitrophenylester of succinoylaminopropyl silica gel having a ligand covalently bound thereto as the affinity matrix.
4. The method of claim 3 wherein the silica gel affinity matrix has an average particle diameter of from about 3 to about 70 microns.
5. The method of claim 3 wherein the ligand is a protein containing an amine group reactive with the affinity matrix.
6. The method of claim 4 wherein the ligand is a protein containing an amine group reactive with the affinity matrix.

* * * * *